(12) United States Patent
Schmid

(10) Patent No.: US 9,357,919 B2
(45) Date of Patent: Jun. 7, 2016

(54) METHOD AND DEVICE FOR ALIGNMENT OF AN OPTICAL IMAGING SYSTEM

(71) Applicant: Novartis AG, Basel (CH)

(72) Inventor: Stefan Schmid, Heilsbronn (DE)

(73) Assignee: Novartis AG (CH)

( * ) Notice: Subject to any disclaimer, the term of this patent is extended or adjusted under 35 U.S.C. 154(b) by 0 days.

(21) Appl. No.: 14/529,093

(22) Filed: Oct. 30, 2014

(65) Prior Publication Data
US 2015/0124256 A1 May 7, 2015

(30) Foreign Application Priority Data
Nov. 5, 2013 (DE) .......................... 10 2013 018 547

(51) Int. Cl.
| | | |
|---|---|---|
| G01B 11/00 | (2006.01) | |
| A61B 3/15 | (2006.01) | |
| G01B 21/00 | (2006.01) | |
| G01B 9/00 | (2006.01) | |
| G01B 11/02 | (2006.01) | |
| G01B 11/27 | (2006.01) | |

(52) U.S. Cl.
CPC . *A61B 3/152* (2013.01); *G01B 9/00* (2013.01); *G01B 11/026* (2013.01); *G01B 11/272* (2013.01); *G01B 21/00* (2013.01)

(58) Field of Classification Search
CPC ........... G03F 9/70; G03F 9/7088; G03F 9/00; G01B 11/272; H01L 21/681
USPC ........................................................ 356/400
See application file for complete search history.

(56) References Cited

U.S. PATENT DOCUMENTS

| | | |
|---|---|---|
| 5,568,257 A | 10/1996 | Ota et al. |
| 5,661,816 A | 8/1997 | Fantone et al. |
| 9,101,300 B2 * | 8/2015 | Endo .......................... A61B 3/14 |
| 2002/0154215 A1 * | 10/2002 | Schechterman ... A61B 1/00193 348/51 |
| 2003/0021603 A1 | 1/2003 | Engel |
| 2004/0210108 A1 * | 10/2004 | Shimizu ............. A61B 1/00188 600/112 |
| 2007/0030450 A1 * | 2/2007 | Liang ........................ A61B 3/14 351/206 |
| 2007/0103701 A1 | 5/2007 | Yamashita |
| 2010/0091283 A1 | 4/2010 | Marioni |
| 2012/0038979 A1 * | 2/2012 | Hing ..................... G02B 21/247 359/383 |
| 2014/0002795 A1 * | 1/2014 | Yoshino ................... A61B 3/12 351/206 |
| 2014/0111770 A1 * | 4/2014 | Ohta ........................ A61B 3/14 351/208 |

FOREIGN PATENT DOCUMENTS

| | | |
|---|---|---|
| DE | 261852 | 9/1988 |
| DE | 102009009062 A1 | 9/2010 |
| EP | 1434030 A2 | 6/2004 |
| JP | 2009-002673 A | 1/2009 |
| JP | 2009-198205 A | 9/2009 |
| JP | 2011230179 A | 11/2011 |

* cited by examiner

*Primary Examiner* — Tarifur Chowdhury
*Assistant Examiner* — Md M Rahman

(57) ABSTRACT

An optical imaging system is to be aligned with its optical axis in relation to a given alignment axis. For this, a radiation beam is emitted from one side of the imaging system along the alignment axis. In the direction of beam propagation, there is located behind the imaging system a pair of diaphragm elements, whose apertures are each covered by a piece of material transparent to the radiation, carrying a plurality of sensor elements arranged in a matrix. The sensor elements furnish information about the measured radiation intensity to a signal processing unit, which can graphically illustrate the current alignment status of the imaging system on a monitor and/or produce an automatic adjustment of the imaging system.

14 Claims, 1 Drawing Sheet

METHOD AND DEVICE FOR ALIGNMENT OF AN OPTICAL IMAGING SYSTEM

CROSS REFERENCE TO RELATED APPLICATION

Figure 1:
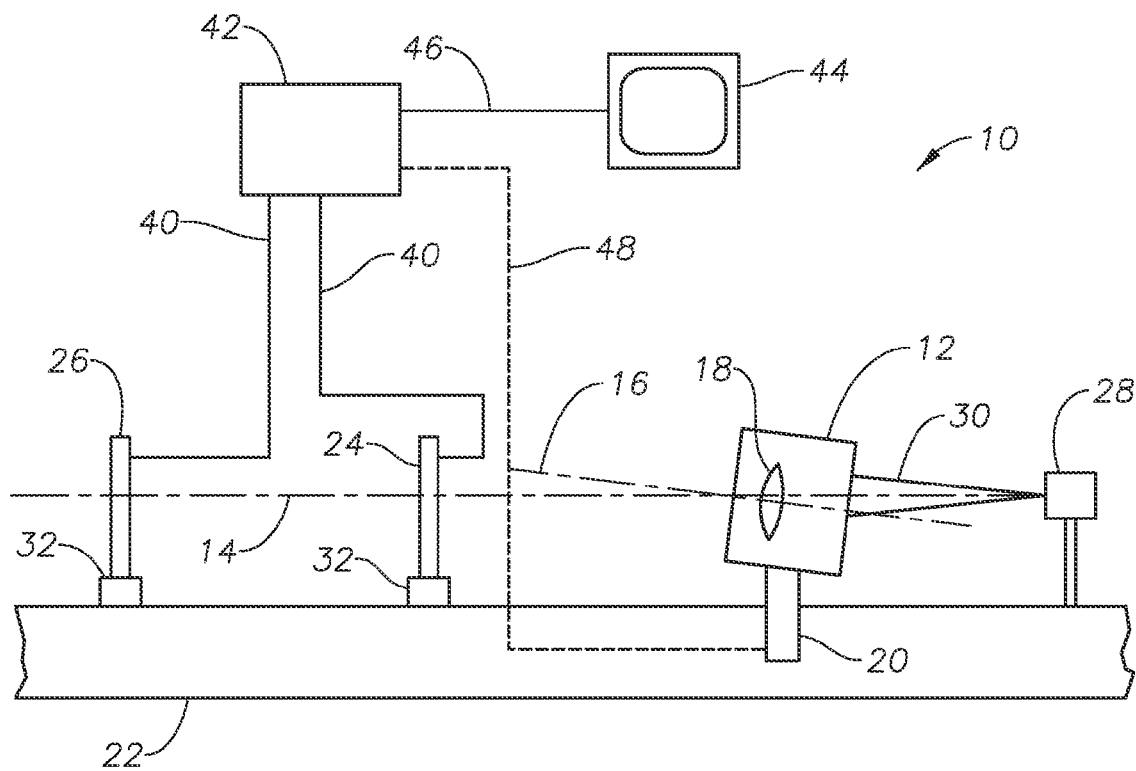

This application claims priority to German Patent Application Serial No. 102013018547.5, filed Nov. 5, 2013, the entire contents of which are incorporated herein by reference.

The present disclosure deals with the alignment of an optical imaging system.

Optical imaging systems are found in numerous instruments of ophthalmology, whether for diagnostics or for treatment. An optical imaging system can have focusing functions, for example, as in a laser instrument, in order to focus the laser radiation used for the treatment of the eye on a point in or on the eye. Also a beam expanding telescope (beam expander), such as is used in many laser devices for expanding a laser beam, can be an optical imaging system, which needs to be aligned. Lenses for imaging an object onto a screen sensor can likewise be optical imaging systems in the sense of the present disclosure. In general, the present disclosure is not limited to lenses for ophthalmology instruments, such as are typically found at an eye doctor's office or an eye clinic. An application in devices outside this field is likewise possible.

The starting point of the present disclosure is the often occurring need to align an optical imaging system precisely with respect to a given axis (hereinafter, alignment axis), which may be dictated, for example, by structural features of the device in which the imaging system is installed or should be installed, such as an assembly rail serving to install at least part of the optical components of the device. The alignment involves adjusting an optical axis of the imaging system in a particular desired manner, typically parallel, with respect to the alignment axis. For this, it must be possible to move the imaging system very delicately with respect to the alignment axis and—once the desired end position is reached—to lock it in the end position.

For the alignment of an optical imaging system one can use, for example, two diaphragm elements arranged at a mutual spacing. The diaphragm elements are fixed to the device so that the alignment axis with respect to which the imaging system is being aligned runs through the apertures of the diaphragm elements. One can even say that the diaphragm elements with their apertures define the alignment axis for purposes of the alignment process. The diaphragm elements, which are either removed entirely or at least folded out from the optical beam path of the device after the alignment has been done, are located on one side of the imaging system, specifically, at the image side. From the other side (object side) of the imaging system, a light beam is emitted along the alignment axis onto the imaging system. For a procedure based solely on the visual observation of the person performing the alignment, the light beam must be in the visible spectrum. The aligning person will move the imaging system relative to the alignment axis (and consequently relative to the two diaphragm elements) until he or she observes that light of the light beam passes not only through the aperture of the first, closer diaphragm element, but also through the aperture of the second, farther diaphragm element. Thus, the light beam must first strike the first diaphragm aperture and then the correct angle position of the imaging system must be adjusted so that the light also strikes the second diaphragm aperture. This can be a difficult and slow and tedious process for the aligning person, because it is easily possible that he or she in seeking the second diaphragm aperture will lose the alignment in relation to the second diaphragm aperture once again.

As compared to this, by one aspect of the invention a method is provided for the alignment of an optical imaging system, comprising defining of an alignment axis at least making use of a first diaphragm element, wherein the alignment axis connects an aperture of the first diaphragm element to a target located at a distance behind the first diaphragm element, aligning of the optical imaging system relative to the alignment axis until radiation of a beam emitted along the alignment axis onto the imaging system after passing through the imaging system strikes the target through the aperture of the first diaphragm element, performing a first sensor detection of radiation in regard to the radiation of the beam at least in the area of the aperture of the first diaphragm element and/or the target, providing of sensor signals generated during the radiation detection for a signal processing unit.

According to one sample modification, image data for a display image is generated by the signal processing unit on the basis of the sensor signals. By means of suitable visualizations on the display image, the person doing the alignment can easily identify, for example, the current position of the beam being used relative to the aperture of the first diaphragm element and/or relative to the target (depending on where the radiation detection is being done) and thus the current alignment status of the imaging system. A visualization of the current alignment status on a monitor can facilitate and shorten the alignment work of the person performing the alignment.

Alternatively or additionally, control signals can be generated by the signal processing unit on the basis of the sensor signals for an actuator for alignment of at least one part of the optical imaging system. In this way, an at least partial automation of the alignment process is possible, which further eases the burden on the person performing the alignment.

The sensor radiation detection can be done solely in the region of the diaphragm aperture with regard to the first diaphragm element. But it is likewise possible for the sensor radiation detection to be done also outside of the diaphragm aperture with regard to the first diaphragm element.

In one embodiment of the invention, the target of one diaphragm aperture is formed by a second diaphragm element. The sensor radiation detection in regard to this second diaphragm element can be done solely in the region of the diaphragm aperture or it can also be done outside of the diaphragm aperture. To form the target, alternatively to a diaphragm element one can use a target surface without diaphragm aperture, for example, with one or more sensors being arranged on the target surface to detect the radiation impinging on the target surface (insofar as radiation gets through the first diaphragm element).

Thanks to the sensor-based detection of the alignment status, the beam used can optionally contain radiation in the visible or the invisible spectrum. In particular, it is possible to use a radiation source which may be present any way in the instrument for which the imaging system is intended, even if this does not emit in the visible spectrum, such as a UV or IR laser. But of course a separate radiation source can also be used, one which is not required for the actual operation of the instrument.

The imaging system being aligned can be a lens system, consisting of a single lens or an assembly of lenses.

According to another aspect of the invention a device for alignment of an optical imaging system is provided, comprising a first diaphragm element with a diaphragm aperture, a target element situated at a distance behind the first diaphragm element, defining a target location, a source for a radiation beam, the source being arranged or able to be arranged such that the radiation beam can be emitted onto the first diaphragm element along an alignment axis connecting the aperture of the first diaphragm element to the target location, an alignment support for the imaging system, wherein the alignment support allows an alignment of the imaging system relative to the alignment axis until radiation of the radiation beam after passing through the imaging system strikes the target location through the aperture of the first diaphragm element, a sensor arrangement for radiation detection in relation to radiation of the radiation beam at least in the region of the aperture of the first diaphragm element and/or the target location, a signal processing unit for processing of sensor signals of the sensor arrangement.

According to one embodiment, the sensor arrangement on the first diaphragm element and/or on a second diaphragm element whose aperture forms the target location is only able to detect radiation in the region of the diaphragm aperture.

One advantageous modification calls for the aperture in at least one diaphragm element to be covered by a piece of material transparent to the radiation, and the piece of material carries at least one sensor element for detecting the radiation of the radiation beam. The sensor element can be arranged, for example, in the region of the aperture of the diaphragm element so as to enable a radiation detection in the region of the diaphragm aperture.

In one sample embodiment, the piece of material carries a plurality of sensor elements arranged with a mutual spacing. At least one subset of these sensor elements (that is, two or more) can be arranged in the region of the aperture of the diaphragm element, or if desired all of the sensor elements of the piece of material can be so arranged. The sensor elements can have a regular distribution, in matrix fashion, or they can be distributed irregularly, which can help in reducing or preventing unwanted diffraction effects.

The first diaphragm element can be formed by a diaphragm element fitted with a piece of material and a sensor element. Alternatively or additionally, the target can be formed on a diaphragm element fitted with a piece of material and a sensor element.

The signal processing unit can be connected to a display unit, the signal processing unit being adapted to generating image data for a display image on the basis of the sensor signals and displaying the display image on the display unit.

Alternatively or additionally, the signal processing unit can be connected to an actuator for the imaging system, the signal processing unit being adapted to generating control signals for the actuator on the basis of the sensor signals for the alignment of at least part of the optical imaging system.

For further investigations, such as the surveying of beam paths outside the optical axis of the imaging system, the size of the aperture of the first diaphragm element and/or a second diaphragm element forming the target location can be changeable. For example, a manual adjustment possibility can be present, or the diaphragm size can be controlled by the signal processing unit in the context of a further automation.

Figure 2:
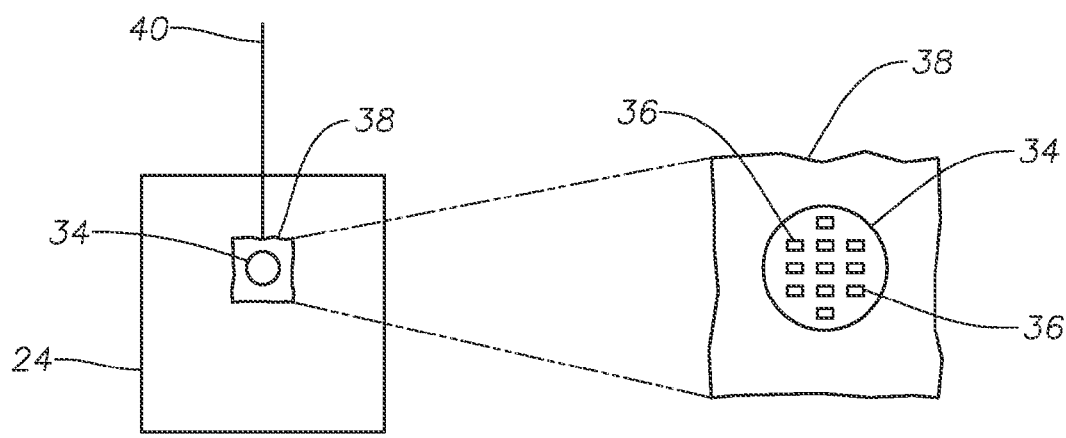

The invention shall now be explained more closely by means of the enclosed schematic drawings. There are shown:

FIG. 1, a sample embodiment of a device for alignment of an optical imaging system and FIG. 2, a diaphragm element of the device of FIG. 1, outfitted with sensors for beam detection, in magnified view.

The alignment device shown in FIG. 1 is designated overall as 10. It allows the aligning of an optical imaging system—represented schematically by a box 12—relative to a given alignment axis 14, i.e., to adjust the imaging system 12 in space so that an optical axis 16 of the imaging system 12 has a certain desired position and orientation with respect to the alignment axis 14. As a rule, the purpose of the alignment is to adjust the imaging system 12 so that its optical axis 16 runs parallel and in particular coaxially to the alignment axis 14.

The imaging system 12 can have any given number of optical lenses, which can be moved as a unit relative to the alignment axis 14. Accordingly, the imaging system 12 can be designed as a single-lens system or a multiple-lens system. Purely for purposes of illustration, FIG. 1 shows a single lens 18; but this is in no way to be viewed as a limitation. If desired, the optical imaging system 12 can alternatively or additionally comprise one or more other optical elements, such as diffractive elements.

The imaging system 12 is supported by an alignment support 20 on a mounting base 22, shown only schematically in FIG. 1. The mounting base 22 serves to support various optical components of the alignment device 10, including a pair of diaphragm elements 24, 26 and a radiation source 28, which is able to emit a radiation beam 30 with a beam axis parallel, preferably coaxial, to the alignment axis 14. In relation to the direction of propagation of the radiation beam 30, the mounting position of the radiation source 28 is located in front of the imaging system 12 being aligned, while the mounting positions of the pair of diaphragm elements 24, 26 lie behind the imaging system 12. The mounting base 22 is part of an ophthalmological diagnostic or treatment instrument. Besides the imaging system 12, the radiation source 28 and the diaphragm pair 24, 26, other optical components are secured or can be secured to the mounting base 22, which are not needed for purposes of the alignment of the imaging system 12, but required for the functioning of the diagnostic or treatment instrument. For example, one or more deflecting mirrors, components of a scanner, one or more cameras, components of an optical coherence tomography (OCT) or optical low-coherence reflectometry (OLCR) measuring device and the like are or can be additionally arranged on the mounting base 22. Such additional optical components are well known to the persons skilled in the art and need no further description here.

The mounting base 22 can have a rail shape, for example, but it can also have any other more complex geometry.

The alignment support 20 enables a manual and/or electrically controlled movement of the imaging system 12 relative to the mounting base 22. The alignment axis 14 has a predetermined position and orientation relative to the mounting base 22, so that an adjustment of the imaging system 12 relative to the mounting base 22 at the same time entails an adjustment relative to the alignment axis 14. The alignment support 20 for example can enable a swiveling of the imaging system 12 about one or more pivot axes relative to the mounting base 22. Alternatively or additionally, the alignment support 20 can enable a translatory movement of the imaging system 12 in one or more directions of translation relative to the mounting base 22.

The diaphragm elements 24, 26 are each fixed to the mounting base 22 via a diaphragm holder 32. Since the diaphragm elements 24, 26 are needed only for alignment purposes, but not for the actual diagnostic or treatment operation of the instrument in which the imaging system 12 in installed, the diaphragm holders 32 enable a removal of the diaphragm elements 24, 26 from the area of the optical axis 16 of the—aligned—imaging system 12. For this, the diaphragm holders 32 can enable, for example, a detachable fixation of the diaphragm elements 24, 26 to the mounting base 22, as in a plug in or screwing fashion. Alternatively, it is conceivable for the diaphragm holders 32 to enable a swiveling or some other path of motion of the diaphragm elements 24, 26, so that they do not disrupt the actual diagnostic or treatment process. Such a swiveling or other movement of the diaphragm elements 24, 26 can be done manually or the diaphragm holders 32 can be electrically actuated and designed with suitable drive means (such as electric motors) to enable an automated placement of the diaphragm elements 24, 26 in and out of use.

The radiation source 28 emits radiation in the visible and/or invisible spectrum. It can be a radiation source also needed for the diagnostic and/or therapeutic operation of the ophthalmological instrument. Alternatively, it can be an auxiliary radiation source not required for the operation of the ophthalmological instrument, which remains shut off during the main operation of the ophthalmological instrument or can even be dismounted from the mounting base 22. If desired, the radiation source 28, like the diaphragm elements 24, 26, can be arranged on the mounting base 22 able to move (such as by swiveling) between a position of use and a position out of use. The radiation can be generated in the radiation source 28 itself; alternatively, it is conceivable for the radiation source 28 to form only a delivery head for radiation which is generated elsewhere in the alignment device 10 or the ophthalmological instrument (insofar as the radiation source 28 is also used in the ophthalmological instrument) and supplied to the delivery head, for example, by an optical fiber or by a radiation arm.

The mutual spacing of the diaphragm elements 24, 26 in the direction of the alignment axis 14 is, for example, a few centimeters or a few tens of centimeters. A comparable spacing can exist between the imaging system 12 and the first diaphragm element 24 (i.e., the first of the two diaphragm elements 24, 26 in the direction of beam propagation).

Each of the two diaphragm elements 24, 26 has, for example, a circular diaphragm hole 34, see FIG. 2. This figure shows the diaphragm element 24 as a representative, but the following remarks hold equally for the diaphragm element 26, unless differences are expressly pointed out. The diaphragm hole 34 can have a diameter in the range of 0.1 to 2 mm, for example. In the position of use of the diaphragm elements 24, 26, i.e., when performing the alignment of the imaging system 12, the diaphragm apertures 34 of the two diaphragm elements 24, 26 are centered on the alignment axis 14. In other words, the alignment axis 14 runs through the aperture midpoints of the diaphragm apertures 34. The imaging system 12 is correctly aligned when at least portions of the radiation from the radiation beam 30, whose beam axis lies coaxially to the alignment axis 14 and which is emitted from an entry side (object side) into the imaging system 12, pass not only through the diaphragm hole 34 of the first diaphragm element 24, but also these radiation portions arrive in the region of the aperture 34 of the second diaphragm element 26. The radiation beam 30 can be divergent, in which case it preferably has a very slight divergence. Alternatively, it can be a collimated beam without divergence. For example, the radiation beam 30 can be formed from laser light.

In order to detect whether radiation of the radiation beam 30 is impinging on the apertures 34 of the two diaphragm elements 24, 26, each of the two diaphragm elements in the sample embodiment shown is outfitted with suitable sensors in order to detect the impinging of radiation of the radiation beam 30 in the region of the particular diaphragm aperture 34.

As is shown in FIG. 2 on the example of the diaphragm element 24, an arrangement of several sensor elements 36 sensitive to the radiation of the radiation beam 28 is located inside the region of the diaphragm aperture 34, being distributed in a two-dimensional grid pattern in the example shown. The sensor elements 36 do not fill up the entire aperture cross section of the diaphragm aperture 34, at least in the case of the diaphragm element 24, but instead leave gaps between each other and also at the margin of the diaphragm aperture 34. These gaps enable the passage of radiation of the radiation beam 30 through the diaphragm aperture 34. In an alternative embodiment, only a single sensor element 36 can be present within the periphery of the diaphragm aperture 34.

In the example shown in FIG. 2, sensor elements 34 are found only inside the circumference of the diaphragm aperture 34, but not outside it. However, it is not ruled out in the context of the invention to also arrange one or more sensor elements outside the diaphragm aperture 34.

The carrier of the sensor elements 36 is a piece of material 38 at least partly transparent to the radiation of the radiation source 28, completely covering the diaphragm aperture 34 and fastened to the diaphragm element 24, for example, by gluing, or otherwise. The piece of material 38 can be formed from a rigid, i.e., shape-stable material, or it can be formed from a flexible material. As for the thickness of the piece of material, it can be as thin as a film or fashioned in the manner of a plate or disk. For example, the material 38 can consist of glass of PMMA (polymethylmethacrylate) or PE (polyethylene) or PC (polycarbonate). Of course, any transparent or translucent material is suitable to form the piece of material 38, as long as the sensor elements 36 can be provided with the desired position stability. The sensor elements 36 can be glued to the piece of material 38, for example, or applied to it by a lithography method. Advantageously, with a distributed arrangement of several sensor elements 36 on the piece of material 38, it is possible to obtain position-resolved information as to the intensity of the impinging radiation.

Of course, instead of a circular aperture the diaphragm aperture 34 can be a rectangular or square aperture. The sensor elements 36 are preferably distributed as uniformly as possible over the entire cross section of the aperture, regardless of the shape of the diaphragm aperture 34.

The second diaphragm element 26 can be eliminated in one alternative embodiment and be replaced by a different carrier for the sensor elements 36, such as a plate type, without this carrier requiring an opening that serves as a diaphragm. It is enough for the carrier to be outfitted with one or more sensor elements 36 in the region where the alignment axis 14 pierces the carrier. A transparency of the carrier to radiation of the radiation beam 30 is not required. Even if this carrier is not transparent to radiation, information can be gained from the sensor elements 36 as to whether the imaging optics 12 is correctly aligned or not.

The sensor elements 36 deliver their sensor signals via corresponding signal lines 40 to an electronic signal processing unit 42, which processes the sensor signals. The processing can involve a generating of image signals, which can be placed by the signal processing unit 42 on a display unit (monitor) 44 for display. The displayed image can contain a graphic representation of the current alignment status of the imaging system 12 in relation to the alignment axis 14 and/or the diaphragm aperture(s) 34. In the case of a manual alignment of the imaging system 12, such a graphic representation can make the alignment chore easier for the user. An image signal line 46 between the signal processing unit 42 and the display unit 44 serves to transmit the image signals in FIG. 1.

For an automated alignment of the imaging system 12, the signal processing unit 42 can alternatively or additionally generate control signals, which can be sent via a control signal line 48 (shown dotted in FIG. 1) to a servo drive for the imaging system 12, not otherwise shown in the drawn, for example, one which is integrated in the alignment support 20. By comparison with a predetermined nominal status, the signal processing unit 42 can use the currently supplied sensor signals to ascertain a further need for adjustment and to actuate the mentioned servo drive accordingly. The nominal status can be defined, for example, by one or more threshold values for the signal intensity of the sensor signals of the sensor elements 36, while the threshold values can be established specifically for individual sensor elements 36 and/or for one or more groups of the sensor elements 36. Alternatively or additionally, the nominal status can be defined by a predetermined local distribution of the radiation intensity detected by the sensor elements 36. Of course, the mentioned criteria are only examples and if so desired other criteria can be used to establish the nominal status. In certain circumstances, different criteria can be established for the target location (represented in the sample embodiment of FIG. 1 by the diaphragm aperture 34 of the second diaphragm element 26) than for the first diaphragm element 24.

It goes without saying that instead of a wired transmission of the image and control signals by the signal lines 46, 48, a wireless transmission of at least some of these signals, such as by WLAN, WiFi, or Bluetooth, can be considered.

In addition, the aperture 34 of the first diaphragm element 24 and/or the second diaphragm element 26 can be adjustable in size, either manually or controlled by the signal processing unit 42. With an enlarged cross section of the diaphragm aperture 34, one can also measure radiation paths lying outside the optical axis 16. Of course, with an adjustable-size diaphragm aperture 34, the region of the piece of material 38 outfitted with sensor elements 36 is sufficiently large to be able to perform radiation measurements essentially across the entire aperture cross section even at the largest cross section of the diaphragm aperture 34. At least some of the sensor elements 36 will then be outside the margin of the aperture at reduced size of the diaphragm aperture 34. For example, at increased diaphragm aperture 34 it is possible to take measurements regarding the intensity profile and/or the divergence of the radiation beam 30. Furthermore, diffraction at the edge of the first diaphragm aperture 34 (i.e., the aperture 34 of the first diaphragm element 24) can produce a diffraction pattern at the second detector—formed by the sensor elements 36 of the second diaphragm element 26—which can be evaluated by the signal processing unit 42 by means of the sensor signals of this second detector to obtain information as to certain properties of the radiation beam 30.

The invention claimed is:

1. A method for alignment of an optical imaging system, comprising:
    defining an alignment axis with at least a first diaphragm element, wherein the alignment axis connects an aperture of the first diaphragm element to a target located at a distance behind the first diaphragm element, a plurality of sensor elements disposed within a material covering the aperture of the first diaphragm element, the sensor elements arranged in a two-dimensional pattern within the aperture;
    aligning the optical imaging system relative to the alignment axis until radiation of a beam emitted along the alignment axis onto the imaging system after passing through the imaging system strikes the target through the aperture of the first diaphragm element, the material at least partially transparent to the radiation;
    performing, with the sensor elements, a first sensor detection of radiation in regard to the radiation of the beam within the aperture of the first diaphragm element; and
    providing sensor signals generated during the radiation detection to a signal processing unit.

2. The method according to claim 1 wherein the target is formed by a second diaphragm element.

3. The method according to claim 1, further comprising:
    performing sensor radiation detection in regard to the first diaphragm element outside of the diaphragm aperture.

4. The method according to claim 1, further comprising generating, by the signal processing unit, image data for a display image on the basis of the sensor signals.

5. The method according to claim 1, further comprising generating, by the signal processing unit, control signals on the basis of the sensor signals for an actuator to align at least one part of the optical imaging system.

6. A device for alignment of an optical imaging system, comprising:
    a first diaphragm element with a diaphragm aperture,
    a target element situated at a distance behind the first diaphragm element, defining a target location;
    a source for a radiation beam, the source being arranged or able to be arranged such that the radiation beam can be emitted onto the first diaphragm element along an alignment axis connecting the aperture of the first diaphragm element to the target location;
    an alignment support for the imaging system, wherein the alignment support allows an alignment of the imaging system relative to the alignment axis until radiation of the radiation beam after passing through the imaging system strikes the target location through the aperture of the first diaphragm element;
    a sensor arrangement for radiation detection in relation to radiation of the radiation beam at least within the aperture of the first diaphragm element or the target location, the sensor arrangement comprising a plurality of sensor elements disposed within a material covering the aperture of the first diaphragm element, the sensor elements arranged in a two-dimensional pattern within the aperture, the material at least partially transparent to the radiation; and
    a signal processing unit for processing of sensor signals of the sensor arrangement.

7. The device according to claim 6, further comprising a second diaphragm element whose aperture forms the target location.

8. The device according to claim 6, further comprising a second sensor arrangement on a second diaphragm element whose aperture forms the target location.

9. The device according to claim 6, wherein:
    at least the aperture of the diaphragm element is covered by a piece of material transparent to the radiation, and
    the piece of material carries at least one sensor element of the plurality of sensor elements for detecting the radiation of the radiation beam.

10. The device according to claim 9, wherein the piece of material carries the plurality of sensor elements arranged with mutual spacing.

11. The device according to claim 10, wherein the sensor elements are arranged in a matrix.

12. The device according to claim 6, further comprising:
    a display unit coupled to the signal processing unit, the signal processing unit adapted to generate image data for a display image on the basis of the sensor signals and display the display image on the display unit.

13. The device according to claim 6, further comprising an actuator for the imaging system coupled to the signal processing unit, the signal processing unit adapted to generate control signals for the actuator on the basis of the sensor signals to align at least part of the optical imaging system.

14. The device according to claim 6, wherein the size of the aperture of the first diaphragm element or a second diaphragm element forming the target location is changeable.

* * * * *